United States Patent
Rutishauser et al.

(10) Patent No.: US 6,368,561 B1
(45) Date of Patent: Apr. 9, 2002

(54) MAGNETIC SEPARATOR

(75) Inventors: Marcel Rutishauser, Wolfhausen; Ralf Bartl, Rüti, both of (CH)

(73) Assignee: Tecan AG, Hombrechtikon (CH)

(*) Notice: Subject to any disclaimer, the term of this patent is extended or adjusted under 35 U.S.C. 154(b) by 0 days.

(21) Appl. No.: 09/362,535

(22) Filed: Jul. 28, 1999

(30) Foreign Application Priority Data

Jul. 31, 1998 (CH) .............................................. 1619/98

(51) Int. Cl.[7] .............................................. B01D 35/06
(52) U.S. Cl. ........................ 422/99; 210/205; 210/222; 422/65; 422/52
(58) Field of Search ............................ 422/99, 65, 52; 210/205, 695, 222; 436/48, 49

(56) References Cited

U.S. PATENT DOCUMENTS

| | | | |
|---|---|---|---|
| 5,055,408 A | * 10/1991 | Higo et al. | 436/48 |
| 5,147,529 A | * 9/1992 | Lee et al. | 210/695 |
| 5,443,791 A | * 8/1995 | Cathcart et al. | 422/65 |
| 5,599,501 A | * 2/1997 | Carey et al. | 422/64 |
| 5,705,062 A | * 1/1998 | Knobel | 210/205 |
| 5,888,454 A | * 3/1999 | Leistner et al. | 422/52 |
| 5,976,369 A | * 11/1999 | Howe et al. | 210/222 |
| 5,985,153 A | * 11/1999 | Dolan et al. | 210/695 |
| 5,985,671 A | * 11/1999 | Leistner et al. | 436/49 |
| 6,143,578 A | * 11/2000 | Bendele et al. | 436/526 |

* cited by examiner

*Primary Examiner*—Jill Warden
*Assistant Examiner*—Brian Sines
(74) *Attorney, Agent, or Firm*—Notaro & Michalos P.C.

(57) ABSTRACT

A holder (2) for sample liquid containers, e.g. Eppendorf vessels (15), is horizontally displaceable between a working position above a magnetic arrangement (4) and a heating position above a hotplate (5). The latter are supported on a baseplate (3) which can be vertically displaced by means of a lifting device (9) between a lowered passive position and a raised active position in which the magnetic arrangement (4) and the hotplate (5) act on the sample liquid in the Eppendorf vessels (15) and attract ferromagnetic particles suspended there. To improve the interaction between the ferromagnetic particles and the sample liquid, the magnetic arrangement (4) can be transversely moved by a stepping motor (6) between a first position, in which, for example, a magnetic plate (14) acts on a row of Eppendorf vessels (15) from the right side, and a second position, in which said magnetic plate (14) acts on the same row of Eppendorf vessels (15) from the left side.

16 Claims, 6 Drawing Sheets

MAGNETIC SEPARATOR

FIELD OF THE INVENTION

The invention relates to a magnetic separator according to the precharacterizing clause of claim 1. Such magnetic separators are used in chemical and molecular biological analysis for separating specific substances from a solution. Said substances, in a sample vessel or the like, become attached to ferromagnetic particles which are manipulated by means of a magnetic field.

PRIOR ART

EP-A-0 497 448 discloses a magnetic separator of the generic type, having a fixed holder for a titre plate and a magnetic arrangement vertically displaceable between an active position and a passive position by means of four levers actuatable by means of push rods. However, it is not possible to remove the sample liquid within the magnetic separator completely from the vicinity of the magnetic arrangement and to feed it, for example, to a treatment of another type, which however is necessary in the case of many applications. If, for example, the sample liquid is to be heated, a separate heating station must be provided and the titre plate must be moved between the magnetic separator and the heating station. Either this must be done manually, which is not desirable for various reasons, or appropriate transport means must be provided. Any transport means present will be blocked for a relatively long time by the transport of the titre plate and will not be available for other tasks. In addition, the magnetic separator is suitable only for sample liquid containers of one type.

Another magnetic separator is disclosed in U.S. Pat. No. 5,443,791. Here, a washing means which has a heatable and coolable metal plate for holding sample liquid containers, below which plate a vertically displaceable magnetic arrangement is mounted, is provided in the frame of a workstation. This arrangement in which a further function has been integrated in the magnetic separator without spatial separation has the disadvantage that the magnets are exposed to relatively high temperatures, which is harmful especially for permanent magnets and reduces their efficiency. Moreover, the structure of the station is relatively complicated and the suitability is likewise restricted to sample liquid containers of one type.

SUMMARY OF THE INVENTION

It is the object of the invention to provide a magnetic separator in which the sample liquid can be completely removed from the vicinity of the magnetic arrangement.

This object is achieved by the features in the characterizing clause of claim 1. The invention provides a compact magnetic separator which has a relatively simple structure and with which it is possible to subject the sample liquid to other processing steps, in particular to heat it, without troublesome interactions with the magnetic arrangements occurring. The magnetic separator according to the invention can be formed in such a way that all steps required in specific processes can be carried out therein without modules or external transport means additionally being required. It can also be converted by slight modifications, for sample liquid containers of a different type and size, it also being possible to handle relatively large containers.

The magnetic separator according to the invention can be very readily installed in a relatively large workstation with further modules and transport means, such as, for example, a robot arm which is also used for pipetting and otherwise. During the sequences of functions in the magnetic separator, the transport means thereof are not used and are completely available for their other functions.

BRIEF DESCRIPTION OF THE DRAWINGS

The invention is explained in more detail below with reference to FIGS. which merely represent an embodiment.

DESCRIPTION OF THE PREFERRED EMBODIMENTS

Figure 1A:
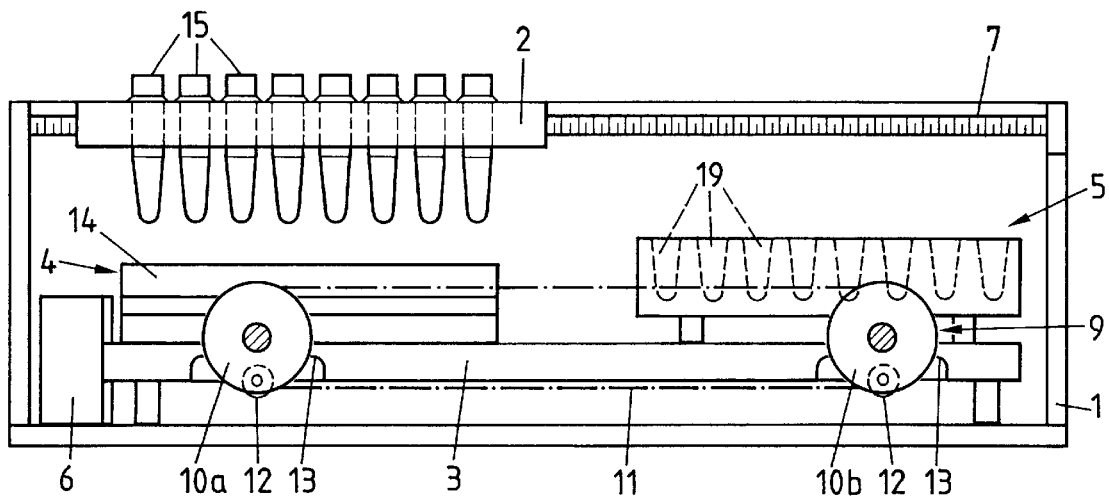
FIG. 1a shows a side view of the magnetic separator according to the invention, with a first type of sample liquid containers in a first setting.

The magnetic separator according to the invention has, in a cuboid housing 1, a holder 2 for sample liquid containers, which is in the form of a frame which surrounds a plurality of orifices superimposed on one another. In the example, there are two intersecting rectangular orifices into which alternatively three different types of sample liquid containers can be inserted, namely 48 Eppendorf vessels in a suitable holder (FIGS. 1a–d, 2a–c) a microtitre plate having 96 vessels (FIGS. 3a–c) or, once again in a suitable holder, 20 test tubes (FIGS. 4, 5a–c). The holder 2 extends over slightly less than half the length of the housing 1.

Below the holder 2 (FIGS. 1a–d, FIGS. 2a–c), a baseplate 3 is arranged in the housing 1, extends essentially over the entire length thereof and, arranged side by side in the longitudinal direction, carries a magnetic arrangement 4 and a heating device in the form of a hotplate 5. In addition to the magnetic arrangement 4, a stepping motor 6 by means of which the magnetic arrangement 4 can be moved transversely to the longitudinal direction is arranged at the end of the baseplate 3. The holder 2 is horizontally displaceable between a working position, in which it is above the magnetic arrangement 4 (FIGS. 1a, b), and a heating position (FIGS. 1c, d), in which it is above the hotplate 5, by means of, for example, a stepping motor via a threaded rod 7 (FIGS. 2a–c) which engages a threaded bush 8 on the holder 2.

The magnetic arrangement 4 and the hotplate 5 are both removable from the baseplate 3 in an upward direction, so that they can be replaced manually or by means of a robot arm. There are three different versions of the magnetic arrangement 4 which are tailored to the three arrangements of sample liquid containers of different type and size (cf. FIGS. 2a–c, FIGS. 3a–c, FIG. 4, FIGS. 5a–c) and two versions of the hotplate 5 which are tailored to the first two types of sample liquid containers, whereas no hotplate is used when handling the third type of sample liquid containers.

The horizontally nondisplaceable baseplate 3 is vertically displaceable, by means of a lifting device 9, between a passive position, in which it is supported on the bottom of the housing 1, lowered relative to the holder 2, and an active position, in which it is relatively just below the holder 2. The lifting device 9 has a pair of gear wheels on each longitudinal side of the housing 1. The gear wheels 10a, b of a pair are each arranged in the vicinity of the opposite ends of the housing 1, are rotatable about axes oriented transversely to the longitudinal direction and are connected by a toothed belt 11 running over them. Each of the gear wheels 10a, b on each longitudinal side has an eccentrically arranged extension, in particular a roller 12, which engages under a downward-facing lifting surface 13 on the baseplate 3.

The toothed belt 11 may furthermore run over a drive wheel driven by a stepping motor, or one of the drive wheels 10a, b itself may be driven. Two gear wheels arranged at the same height on different longitudinal sides of the housing— these may optionally also be the drive wheels—can be connected to one another by a common axle so that only one drive is required. The eccentric rollers 12 are each in their lowest position in the passive position of the baseplate 3 shown in FIG. 1a, and in the highest position in the active position shown in FIG. 1b, in which the baseplate 3 is supported on the rollers 12 by means of the lifting surfaces 13.

The magnetic arrangement 4 has in each case a plurality of magnetic plates 14 extending in the longitudinal direction and a distance apart laterally. The magnetic arrangement 4 suitable for the Eppendorf vessels 15 (cf. FIGS. 2a–c) consists of four such magnetic plates 14 whose lateral spacing is such that two Eppendorf vessels 15 arranged side by side in the holder have space between them. Each magnetic plate 14 consists of two magnetic strips which, separated by a layer of magnetically readily conducting material, are arranged directly side by side and are inclined slightly toward one another in an upward direction, so that they rest against the walls of the Eppendorf vessels 15. They are magnetically oriented toward one another, i.e. approximately transversely to the longitudinal direction of the housing 1, with north poles facing outward and south poles facing toward one another. The poles may also be reversed.

The magnetic arrangement 4 suitable for the microtitre plate 16 (FIGS. 3a–c) has seven individual magnetic plates 14 which are likewise magnetically oriented transversely to the longitudinal direction. The distance between two magnetic plates 14 arranged side by side is once again such that two vessels 17 of the microtitre plate 16 must have space between them.

The same applies to the magnetic arrangement 4 which is suitable for test tubes 18 (FIGS. 4, 5a–c) and has three groups each of three magnetic plates 14 arranged side by side, each of which extends over one third of the length of the magnetic arrangement 4. The middle group is offset relative to the outer groups transversely to the longitudinal direction by half the distance between two adjacent magnetic plates 14 of a group.

The hotplate 5 is a metal plate having indentations 19 for receiving the lower end regions of the sample liquid containers with an exact fit. Said hotplate is electrically heatable by ceramic resistance elements arranged on its lower surface.

As shown in FIGS. 1a–d with Eppendorf vessels 15 as sample liquid containers, there are four basic settings of the magnetic separator. In the first (FIG. 1a), the baseplate 3, and with it the magnetic arrangement 4 and the hotplate 5, is in the passive position, i.e. lowered, so that it is supported on the bottom of the housing 1. The holder 2 is present in a working position in which it is above the magnetic arrangement 4. The magnetic plates 14 are so far away from the Eppendorf vessels 15 that there is virtually no magnetic effect on their content. In the second setting (FIG. 1d), the baseplate 3 is in the active position while the holder 2 still remains in the working position. The magnetic plates 14 each project between two adjacent rows of Eppendorf vessels 15 and touch the latter so that the magnetic field emanating from them has a strong effect on their content.

Figure 1B:
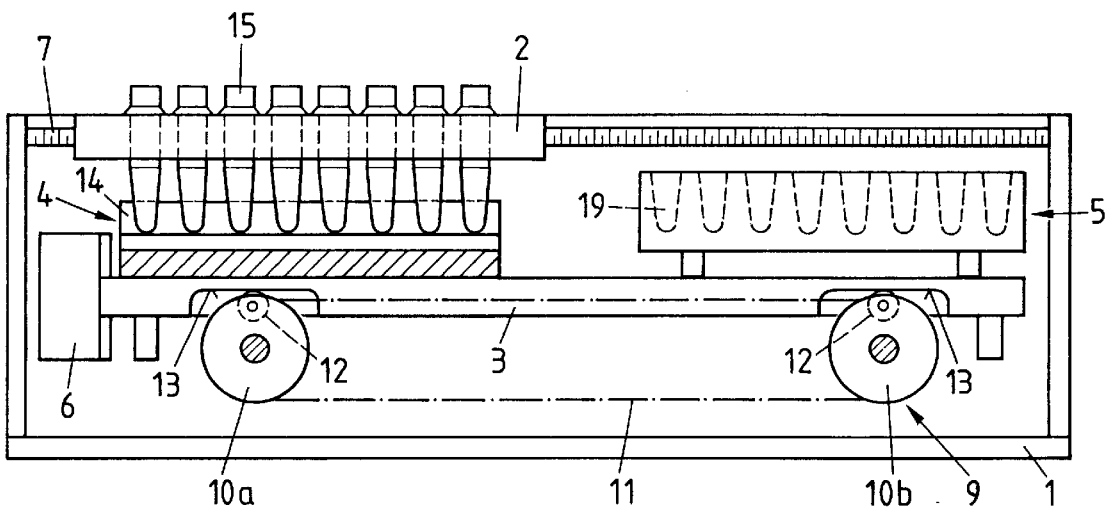
FIG. 1b shows a view corresponding to FIG. 1a, with the magnetic separator in a second setting.
Figure 1C:
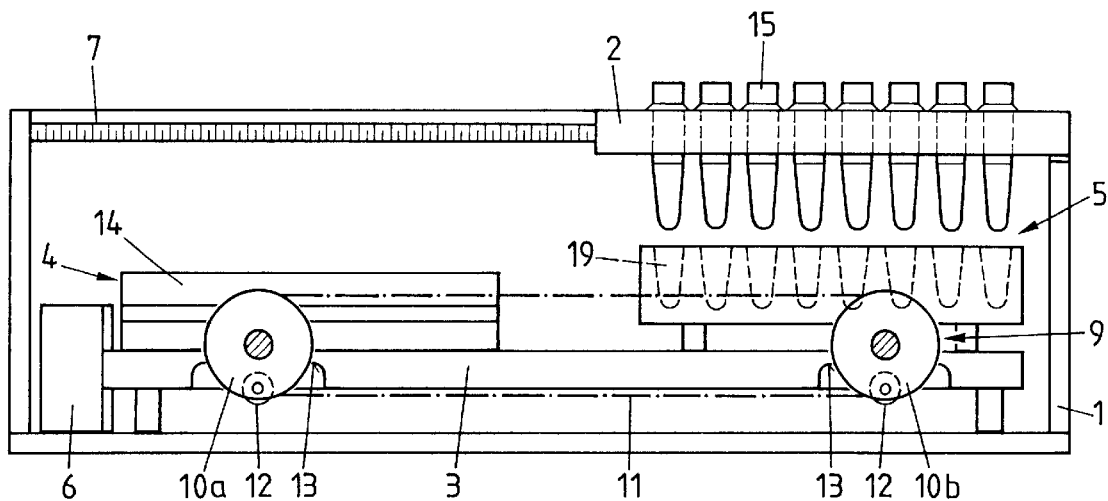
FIG. 1c shows a view corresponding to FIG. 1a, with the magnetic separator in a third setting.
Figure 1D:
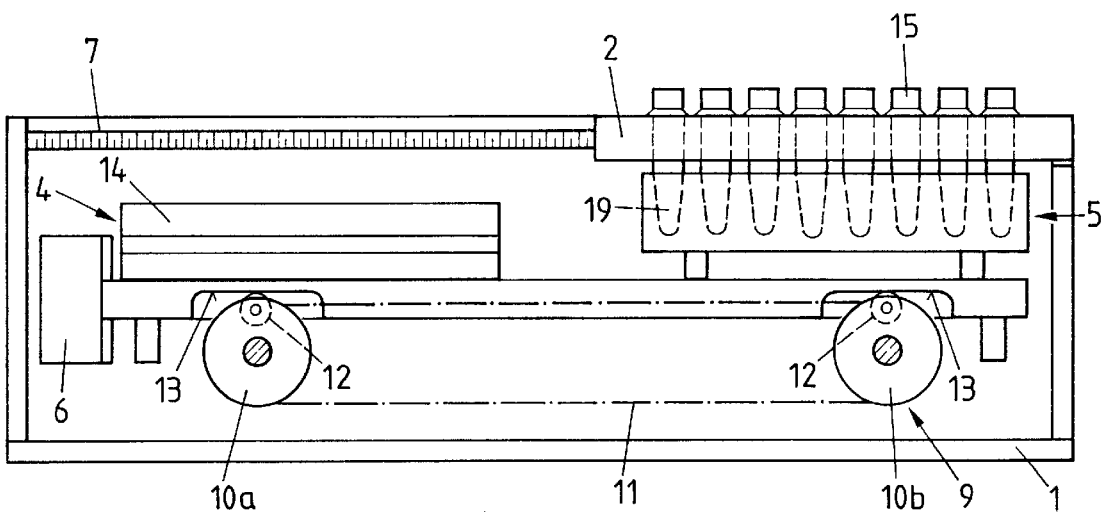
FIG. 1d shows a view corresponding to FIG. 1a, with the magnetic separator in a fourth setting.

After the baseplate 3 has been lowered to the passive position, the holder 2 can be moved to the heating position in which it is above the hotplate 5 (FIG. 1c). If the baseplate 3 is raised again to the active position (FIG. 1d), the indentations 19 of the hotplate 5 receive the lower end regions of the Eppendorf vessels 15. Their content can now be heated. After the baseplate 3 has been lowered to the passive position, the holder 2 can then be moved back to the working position.

Figure 2A:
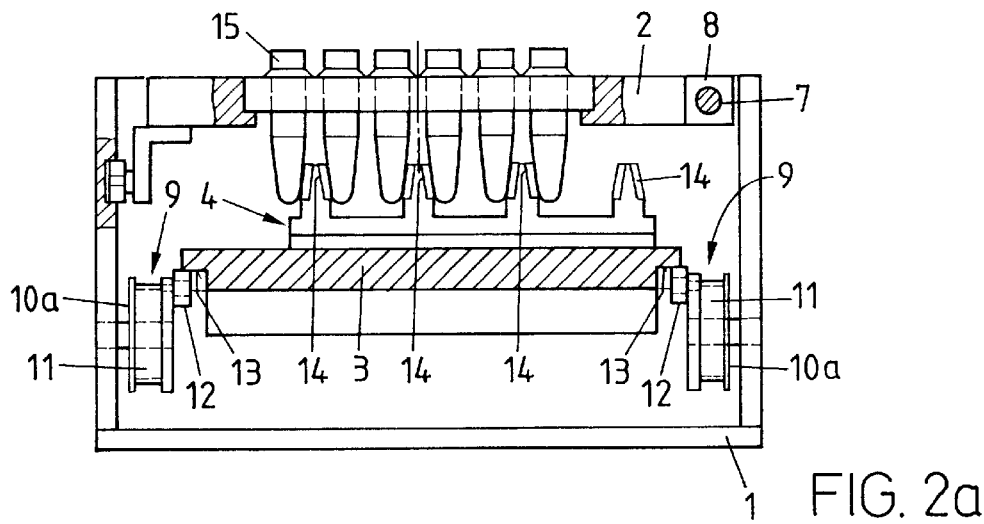
FIG. 2a shows a partially cut away front view with removed housing parts of the magnetic separator according to the invention, in the second setting.
Figure 2B:
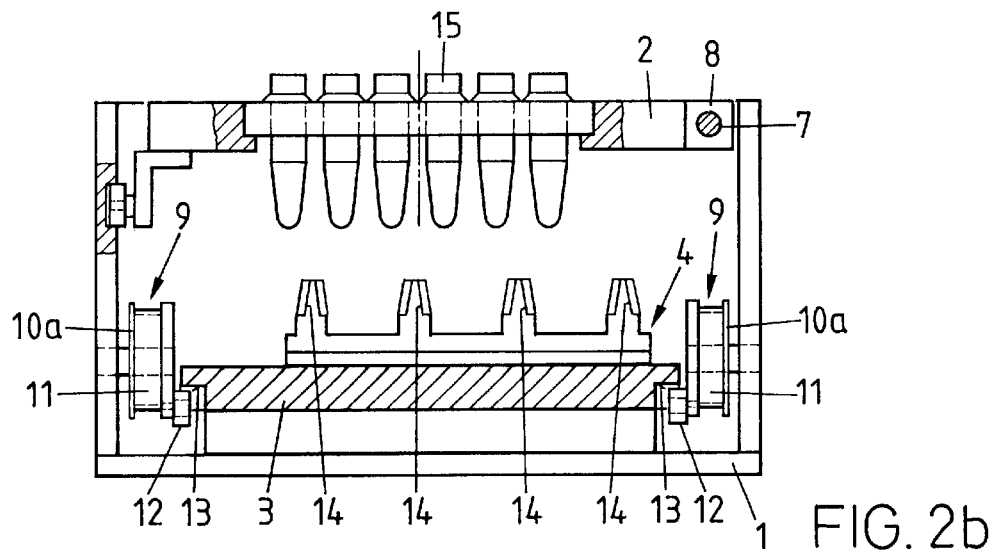
FIG. 2b shows a view, corresponding to FIG. 2a, of the magnetic separator according to the invention, in the first setting.
Figure 2C:
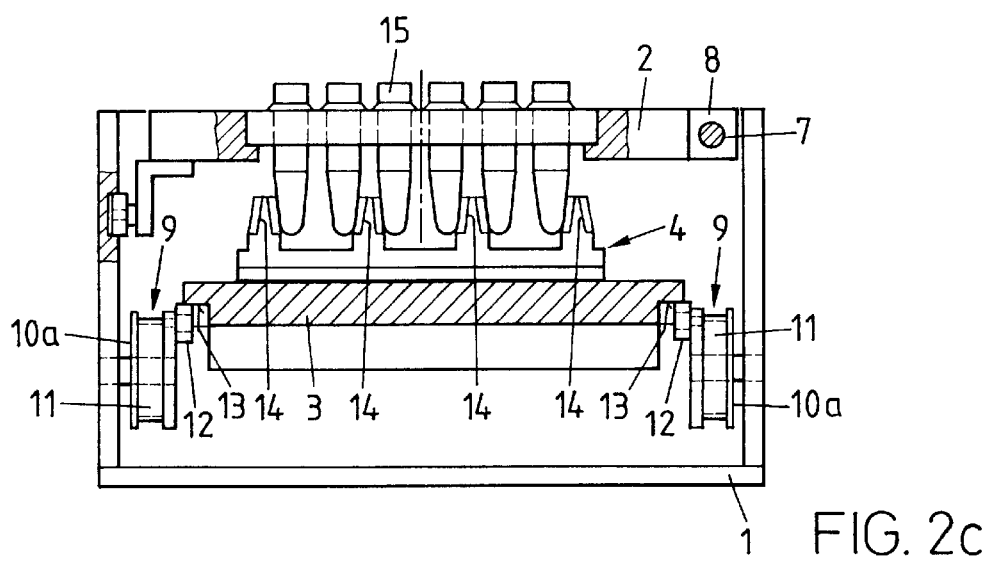
FIG. 2c shows a view, corresponding to FIG. 2a, of the magnetic separator according to the invention, in a modified second setting.
Figure 3A:
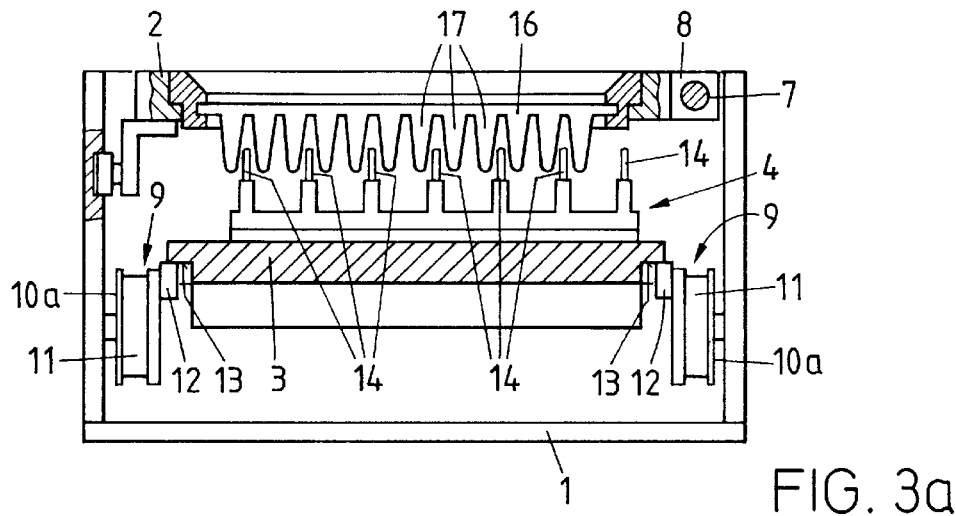
FIG. 3a shows a partially cut away front view with removed housing parts of the magnetic separator according to the invention, with a second type of sample liquid containers, in the second setting.
Figure 3B:
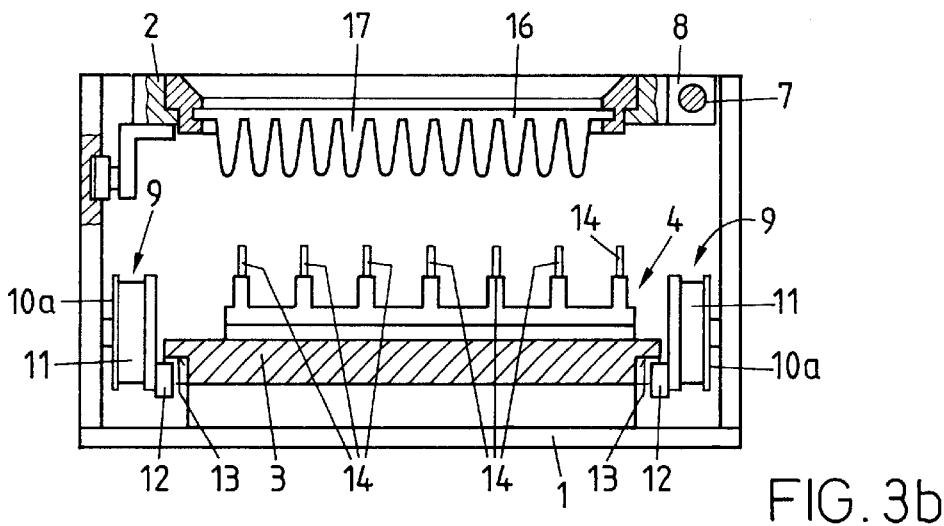
FIG. 3b shows a view, corresponding to FIG. 3a, of the magnetic separator according to the invention, in the first setting.

As shown in FIGS. 2a–c, the magnetic arrangement 4 for the Eppendorf vessels 15 can be moved transversely to the longitudinal direction between two different positions on the baseplate 3, for example by means of the stepping motor 6. The difference between the two positions is such that a magnetic plate 14 which, in the first position (FIG. 2b), was positioned, for example, to the right of a specific row of Eppendorf vessels 15 is positioned to the left of the same row in the second position (FIG. 2c). For changing between the two positions, the magnetic arrangement 4 is in each case lowered to the passive position (FIG. 2b).

Figure 3C:
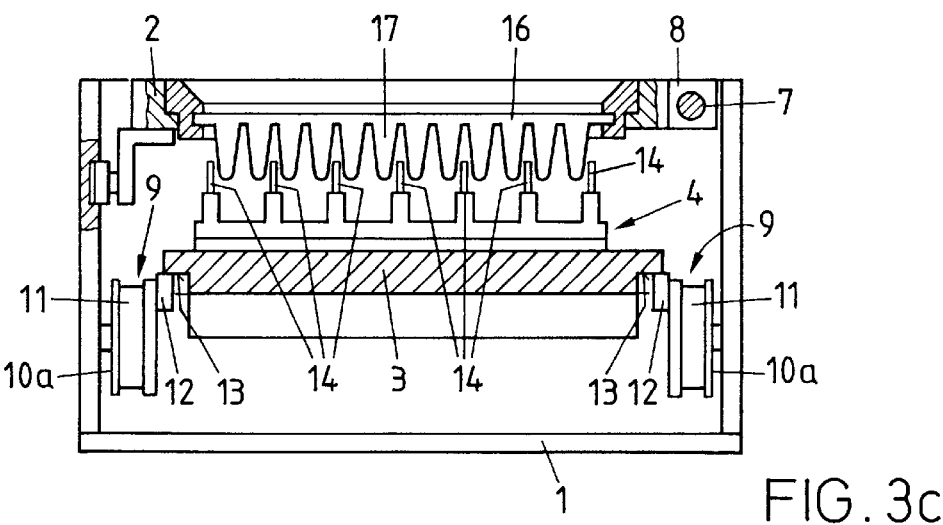
FIG. 3c shows a view, corresponding to FIG. 3a, of the magnetic separator according to the invention, in a modified second setting.
Figure 4:
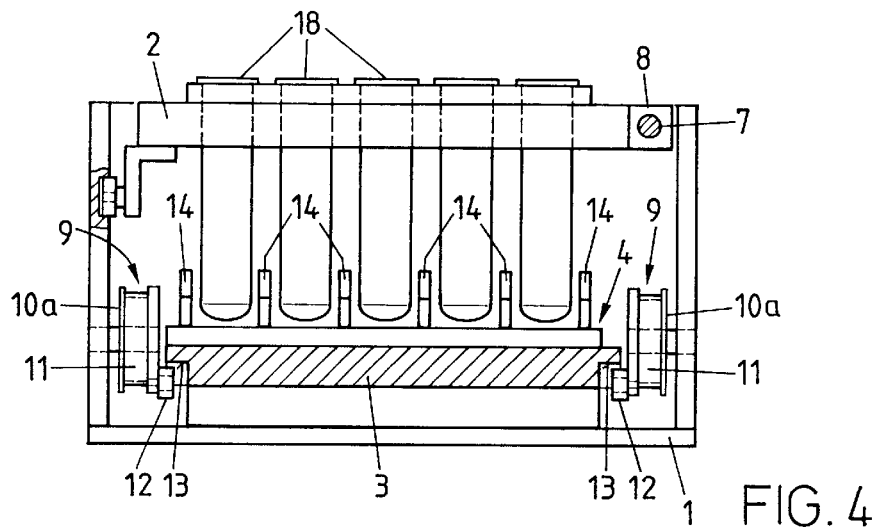
FIG. 4 shows a partial cut away front view with removed housing parts of the magnetic separator according to the invention, with a third type of sample liquid containers.

The magnetic arrangement 4 suitable for the microtitre plate 16 can also be moved transversely in a completely analogous manner by means of the stepping motor 6, between a first and a second position, so that a magnetic plate 14 lying to the right of a specific row of vessels 17 in the first position (FIG. 3a) lies to the left thereof in the second position (FIG. 3c). Here too, the changing of positions is effected in the passive position of the magnetic arrangement 4.

With the use of test tubes 18 and the magnetic arrangement 4 suitable for these, the baseplate 3 always remains in the passive position. In a first setting (FIG. 5a) in which the position of the holder 2 and of the baseplate 3 corresponds to the third setting with the other sample liquid containers, the holder 2 is displaced relative to the magnetic arrangement 4 so that the latter is passive and does not act on the sample liquid in the test tubes 18. In a second setting in which the position of the holder 2 and of the baseplate 3 corresponds completely or almost to the first setting with the other sample liquid containers, the holder 2 is above the magnetic arrangement 4, but, owing to the large length of the test tubes 18, the magnetic plates 14 lie between their lower end regions and act on their content.

Figure 5A:
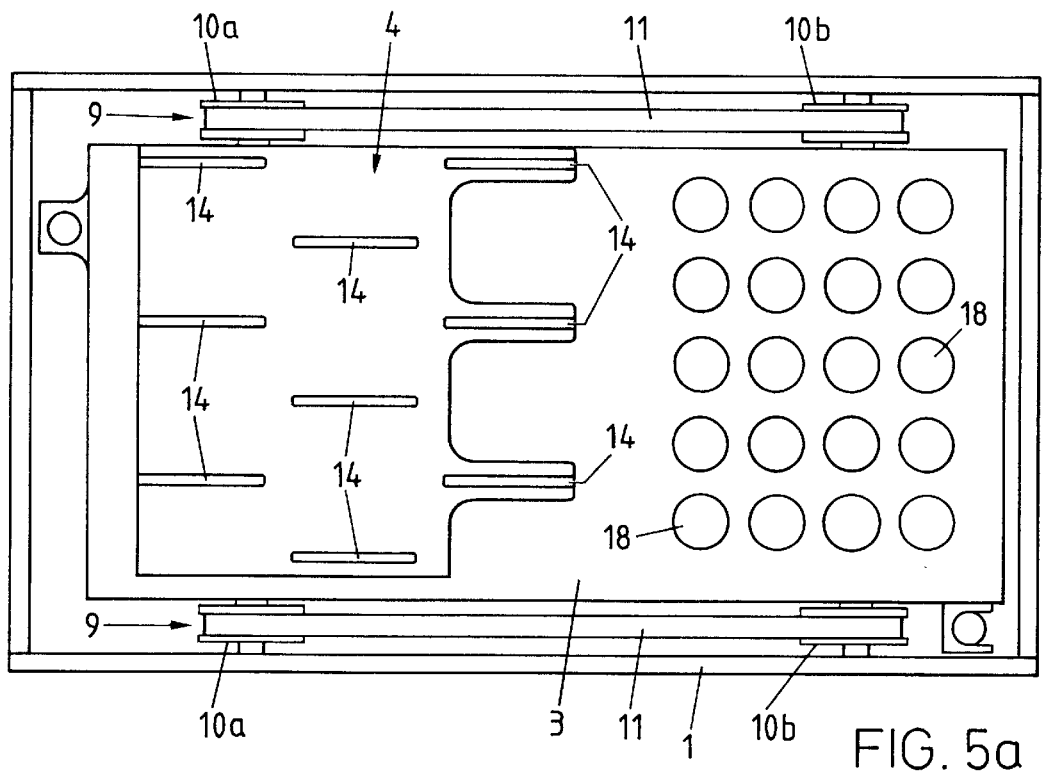
FIG. 5a shows a plan view of the magnetic separator according to the invention, with the third type of sample liquid containers, in a first setting.
Figure 5B:
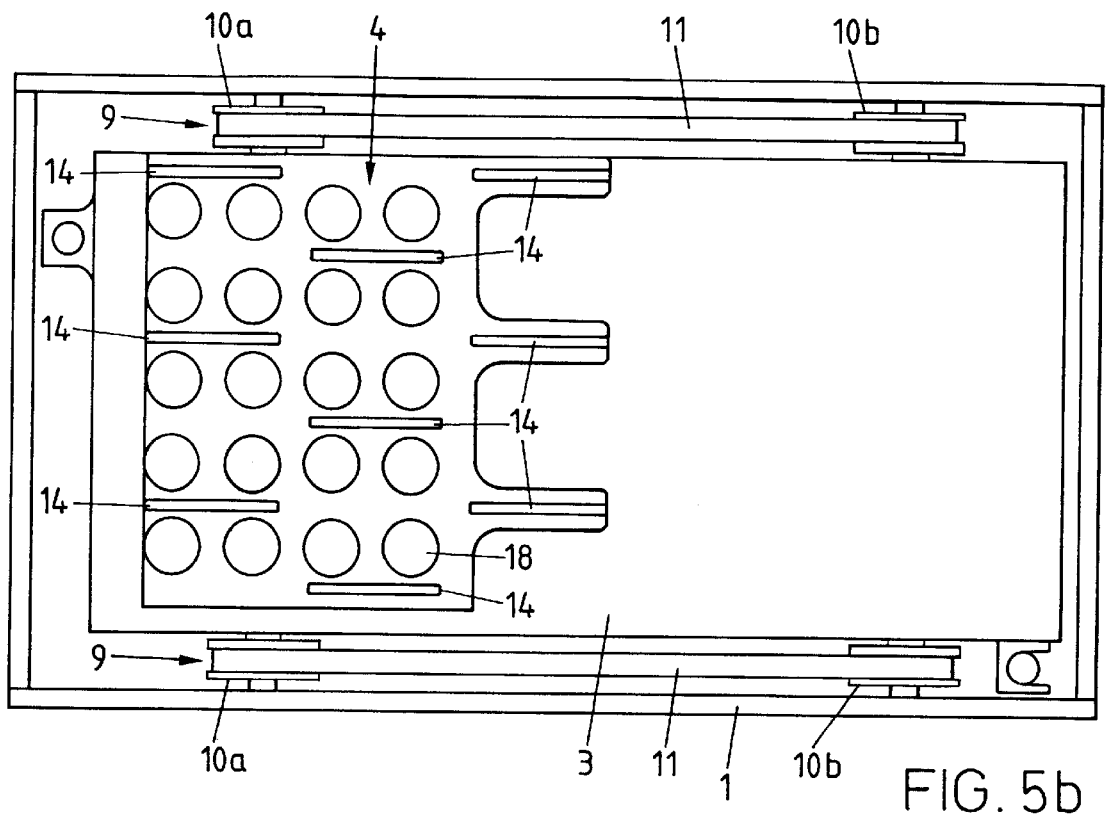
FIG. 5b shows a view, corresponding to FIG. 5a, of the magnetic separator according to the invention, in a second setting.
Figure 5C:
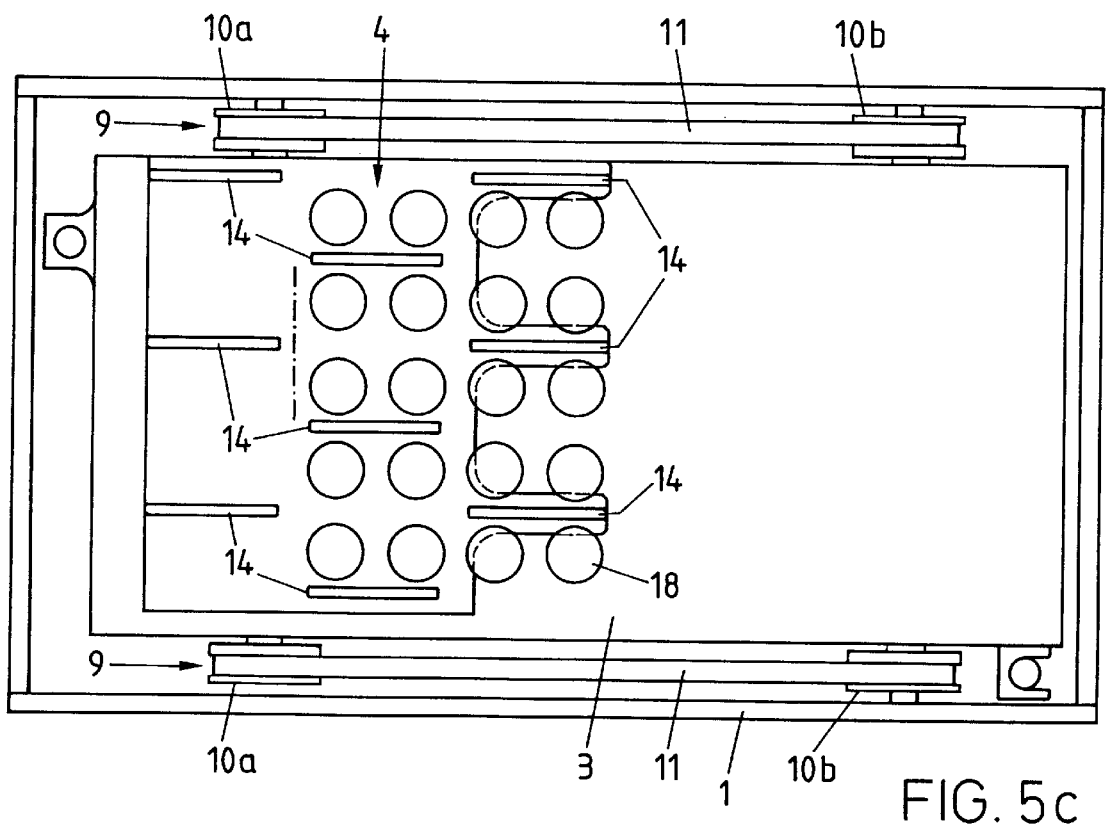
FIG. 5c shows a view, corresponding to FIG. 5a, of the magnetic separator according to the invention, in a modified second setting.

The holder 2 can be moved between a first position (FIG. 5b) and a second position (FIG. 5c). In the first position, the holder 2 is moved completely to that side of the housing 1 which is occupied by the magnetic arrangement 4, so that a first half of the test tubes 18 lies at the height of the outer group of magnetic plates 14 which is adjacent to the end of the housing 1, and the second half at the height of the middle group. In the second position, the holder 2 is displaced in the longitudinal direction so that the first half of the test tubes 18 lies at the height of the middle group of the magnetic plates 14 and the other half at the height of that outer group of magnetic plates 14 which closes off the magnetic arrangement 4 from the middle of the housing 1.

In all cases, the change between the two positions serves for attracting ferromagnetic particles which are suspended in the sample liquid from one lateral wall region of the sample liquid container to the opposite one through the liquid and thus intensifying their interaction with said liquid. In this way, the efficiency with which chemically active substances bind specific components in the sample liquid to their surfaces can be improved, as can the efficiency of the purification of the particles in a wash liquid, both of which will be explained in more detail in the following example of a process carried out in the magnetic separator according to the invention.

In this process, which preferably takes place under computer control and fully automatically, mRNA is isolated from an RNA sample. A holder with 48 Eppendorf vessels 15 is inserted into the holder 2. Elements of the BIOMAG mRNA purification kit from PerSeptive Diagnostics are used for the process. First, 300 µl of BIOMAG Oligo (dT) 20 are pipetted into each of the Eppendorf vessels 15 with the magnetic separator in the first setting (FIG. 1a)—holder 2 in the working position, magnetic arrangement 4 in passive position. This liquid contains ferromagnetic particles whose surface is coated with a substance which specifically binds mRNA. The magnetic separator is then brought into the second setting (FIG. 1b) by raising the baseplate 3 and hence the magnetic arrangement 4 to the active position.

The particles are drawn together in the lateral wall regions closest to each of the magnetic plates 14 by the magnetic field now acting laterally on the Eppendorf vessels 15, slightly above their lower end. The supernatant of the sample liquid is then removed by means of a pipette. An automatic pipetting apparatus having a robot arm can be used for this purpose.

After it was diluted outside the magnetic separator with water, which was treated with DEPC, an antibacterial buffer, and to 270 µl, kept at 55° C. for 5 min and mixed with 30 µl of 5 M NaCl solution, the RNA sample is pipetted into the BIOMAG Oligo dT (20) in the Eppendorf vessels 15. The magnetic arrangement 4 is then moved back and forth several times between the first position (FIG. 2a) and second position (FIG. 2c), said magnetic arrangement being lowered as described to change the position in each case to the passive position (FIG. 2b). As a result, the particles are in each case drawn together several times alternately at opposite wall regions of the Eppendorf vessels 15. They migrate through the sample liquid and have an opportunity of binding the mRNA distributed therein. Finally, with the magnetic arrangement 4 in the active position and accordingly particles drawn together at a wall region, the supernatant is removed as completely as possible by means of a pipette.

The magnetic arrangement 4 is then lowered to the passive position (FIG. 1a), 300 µl of wash buffer are pipetted into the Eppendorf vessels 15 and the magnetic arrangement 4 is raised again to the active position (FIG. 1b). This may be followed by several changes of the magnetic arrangement 4 between the first position (FIG. 2a) and the second position (FIG. 2c). With the magnetic arrangement 4 in the active position, the wash buffer is then removed by means of a pipette. The operation is repeated.

Finally, the magnetic arrangement 4 is lowered to the passive position (FIG. 1b), 75–150 µl of water treated with DEPC are added by means of a pipette and the holder 2 is moved to the heating position (FIG. 1c). After the hotplate 5 has been raised to the active position (FIG. 1d), the samples in the Eppendorf vessels 15 are heated to 55° C. and kept at this temperature for 2 min. As a result of this, the mRNA bound to the particles becomes detached therefrom.

The hotplate 5 is now lowered again to the passive position (FIG. 1c), the holder 2 is moved to the working position (FIG. 1a) and the magnetic arrangement 4 is raised to the active position so that the particles once again collect on a wall region of the Eppendorf vessels 15. The supernatant with the mRNA detached from the particles is then removed by means of a pipette. The treatment of the particles with DEPC/water, the heating and the removal by means of a pipette can be repeated to improve the yield.

The magnetic separator according to the invention can be modified in various ways within the scope of the invention. In particular, only the relative movements of the various parts, such as the holder, the magnetic arrangement and the heating device, are important, and said movements can be effected in various ways. For example, by appropriate formation, it is also possible for the holder to be designed and, by providing further adapted magnetic arrangements and where necessary heating devices, to be supplemented in such a way that further sample liquid containers or sample liquid containers other than those described can be handled. Suitable materials for housing, holder and baseplate are metal, in particular aluminium, possibly also plastic.

List of Reference Symbols

1 Housing
2 Holder
3 Baseplate
4 Magnetic arrangement
5 Hotplate
6 Stepping motor
7 Threaded rod
8 Threaded bush
9 Lifting device
10a, b Gear wheels
11 Toothed belt
12 Roller
13 Lifting surface
14 Magnetic plate 15 Eppendorf vessel
16 Microtitre plate
17 Vessel of the microtitre plate 16
18 Test tube
19 Indentation in the hotplate 5

What is claimed is:

1. A magnetic separator comprising: a holder for at least one sample liquid container; a magnetic arrangement which is arranged underneath said holder and which can be moved, relative to the holder, at least vertically between an active position, in which said magnetic arrangement extends into the immediate vicinity of the at least one sample liquid container, and a passive position, in which said magnetic arrangement is at a distance below said container; said holder being displaceable relative to the magnetic arrangement between a working position, in which said holder lies above the magnetic arrangement, and a further position, in which said holder is horizontally offset relative to the magnetic arrangement; and a heating device arranged adjacent the magnetic arrangement in such a way that the holder, in said further position horizontally offset relative to the magnetic arrangement, occupies a heating position above the heating device.

2. A magnetic separator according to claim 1, wherein said heating device is displaceable relative to the holder, at least vertically between an active position in which said heating device extends into the immediate vicinity of the at least one sample liquid container, and a passive position, in which said heating device is a distance below said container.

3. A magnetic separator according to claim 1, including a housing in which the magnetic arrangement and the heating device are installed in a vertically displaceable manner, and the holder is installed in a horizontally displaceable manner.

4. A magnetic separator according to claim 1, including at least one lifting device with at least one lever which is rotatable about a horizontal axis and engages with an extension under a horizontal lifting surface while the magnetic arrangement and the heating device are vertically guided, for vertical displacement of the magnetic arrangement and of the heating device.

5. A magnetic separator according to claim 4, wherein the lever is in the form of a gear wheel driven by a toothed belt running over said gear wheel.

6. A magnetic separator according to claim 1, wherein the magnetic arrangement has a plurality of at least approximately vertical magnetic plates which extend over the length of the magnetic arrangement.

7. A magnetic separator according to claim 6, wherein the magnetic plates have limited transverse displaceability.

8. A magnetic separator according to claim 1, wherein the magnetic arrangement is arranged on an only vertically displaceable baseplate and is transversely displaceable relative to the only vertically displaceable baseplate.

9. A magnetic separator according to claim 1, wherein the heating device is in the form of a hotplate having indentations in the surface of the hotplate.

10. A magnetic separator according to claim 9, wherein the hotplate comprises metal and electric heating elements mounted on a lower surface of the hotplate.

11. A magnetic separator according to claim 8, wherein the heating device is arranged on the baseplate.

12. A magnetic separator according to claim 1, wherein the magnetic arrangement and the heating device can be removed in an upward direction.

13. A magnetic separator according to claim 1, wherein the holder is in the form of a frame which at least partly surrounds a plurality of orifices of different format which are superimposed on one another.

14. A magnetic separator comprising: a holder for at least one sample liquid container; a magnetic arrangement which is arranged underneath said holder and which can be moved, relative to the holder, at least vertically between an active position, in which said magnetic arrangement extends into the immediate vicinity of the at least one sample liquid container, and a passive position, in which said magnetic arrangement is at a distance below said container; said holder being displaceable relative to the magnetic arrangement between a working position, in which said holder lies above the magnetic arrangement, and a further position, in which said holder is horizontally offset relative to the magnetic arrangement; a heating device arranged adjacent the magnetic arrangement in such a way that the holder, in said further position horizontally offset relative to the magnetic arrangement, occupies a heating position above the heating device; and a housing in which the magnetic arrangement and the heating device are installed in a vertically displaceable manner, and the holder is installed in a horizontally displaceable manner.

15. A magnetic separator comprising: a holder for at least one sample liquid container; a magnetic arrangement which is arranged underneath said holder and which can be moved, relative to the holder, at least vertically between an active position, in which said magnetic arrangement extends into the immediate vicinity of the at least one sample liquid container, and a passive position, in which said magnetic arrangement is at a distance below said container, the magnetic arrangement have a plurality of at least approximately vertical magnetic plates which extend over the length of the magnetic arrangement; said holder being displaceable relative to the magnetic arrangement between a working position, in which said holder lies above the magnetic arrangement, and a further position, in which said holder is horizontally offset relative to the magnetic arrangement; and a heating device arranged adjacent the magnetic arrangement in such a way that the holder, in said further position horizontally offset relative to the magnetic arrangement, occupies a heating position above the heating device.

16. A magnetic separator comprising: a holder for at least one sample liquid container, the holder being in the form of a frame which at least partly surrounds a plurality of orifices of different format which are superimposed on one another; a magnetic arrangement which is arranged underneath said holder and which can be moved, relative to the holder, at least vertically between an active position, in which said magnetic arrangement extends into the immediate vicinity of the at least one sample liquid container, and a passive position, in which said magnetic arrangement is at a distance below said container; said holder being displaceable relative to the magnetic arrangement between a working position, in which said holder lies above the magnetic arrangement, and a further position, in which said holder is horizontally offset relative to the magnetic arrangement; and a heating device arranged adjacent the magnetic arrangement in such a way that the holder, in said further position horizontally offset relative to the magnetic arrangement, occupies a heating position above the heating device.

* * * * *